US006180752B1

(12) United States Patent
Joentgen et al.

(10) Patent No.: US 6,180,752 B1
(45) Date of Patent: Jan. 30, 2001

(54) POLYASPARAGINIC ACID HOMOPOLYMERS AN COPOLYMERS, BIOTECHNICAL PRODUCTION AND USE THEREOF

(75) Inventors: Winfried Joentgen, Köln; Torsten Groth, Odenthal; Alexander Steinbüchel, Altenberge; Tran Hai, Münster; Fred Bernd Oppermann, Hamm, all of (DE)

(73) Assignee: Bayer AG, Levekusen (DE)

( * ) Notice: Under 35 U.S.C. 154(b), the term of this patent shall be extended for 0 days.

(21) Appl. No.: 09/380,659

(22) PCT Filed: Mar. 4, 1998

(86) PCT No.: PCT/EP98/01195

§ 371 Date: Sep. 2, 1999

§ 102(e) Date: Sep. 2, 1999

(87) PCT Pub. No.: WO98/39090

PCT Pub. Date: Sep. 11, 1998

(30) Foreign Application Priority Data

Mar. 6, 1997 (DE) ............................. 197 09 024

(51) Int. Cl.⁷ ............................ C08G 69/00; C08G 73/06
(52) U.S. Cl. ........................ 528/328; 528/332; 528/342; 528/363; 525/420; 525/451; 252/175; 252/363.5
(58) Field of Search ................... 528/363, 328, 528/332, 342; 525/420, 451; 252/145, 363.5

(56) References Cited

U.S. PATENT DOCUMENTS

| 2,895,882 | 7/1959 | Thorne et al. ........................ 195/96 |
| 4,534,881 | 8/1985 | Sikes et al. .......................... 252/180 |
| 4,585,560 | 4/1986 | Sikes et al. .......................... 210/698 |
| 4,587,021 | 5/1986 | Wheeler et al. ...................... 210/698 |
| 4,839,461 | * 6/1989 | Boehmke ............................. 528/363 |
| 4,868,287 | 9/1989 | Sikes et al. .......................... 530/324 |
| 5,260,272 | 11/1993 | Donachy et al. ...................... 524/12 |
| 5,543,490 | * 8/1996 | Groth et al. .......................... 528/328 |

FOREIGN PATENT DOCUMENTS

| 0 256 366 | 2/1988 | (EP) . |
| 0 604 813 | 7/1994 | (EP) . |
| 43-24472 | 10/1968 | (JP) . |
| 92/17194 | 12/1992 | (WO) . |

OTHER PUBLICATIONS

Chemical Abstracts 70582z Mar. 15, 1976.*
S. Weiner, Biochemistry. 22 (1983) p. 4139–45 the Month in the Date of Publication is not Available.
C. S. Sikes, A. P. Wheeler in Chem. Aspects of Regulation of Mineralization, Eds. C. S. Sikes, A. P. Wheeler Univ. of South Alabama Publ. Services (1988) p. 15–20 and 53–57 the Month in the Date of Publication is not available.
Kovacs et al, J. Org. Chem. 26 (1961), p. 1084–1091 the Month in the Date of Publication is not Available.
Derwent Abstract (English language) for JP 24472/68 (1968) the Month in the Date of Publication is not Available.

* cited by examiner

*Primary Examiner*—P. Hampton-Hightower
(74) *Attorney, Agent, or Firm*—Connolly Bove Lodge & Hutz LLP

(57) ABSTRACT

The invention relates to the production of polyaspartic acid homo- and copolymers by biotechnological processes and to the use of the resulting products (for influencing the crystallization or agglomeration behavior of sparingly soluble salts or solids in aqueous systems).

7 Claims, No Drawings

POLYASPARAGINIC ACID HOMOPOLYMERS AN COPOLYMERS, BIOTECHNICAL PRODUCTION AND USE THEREOF

BACKGROUND OF THE INVENTION

1. Field of the Invention

The invention relates to the production of polyaspartic acid homo- and copolymers by biotechnological processes and to the use of the resulting products (for influencing the crystallization or agglomeration behavior of sparingly soluble salts or solids in aqueous systems).

2. Description of the Related Art

Crystallization and agglomeration processes are, as biological mineralization, among the fundamental processes of animate nature. Thus, they are involved, for example, in the structure of skeletons or shells in living organisms. In nature, these mineralization processes are controlled by naturally occurring proteins and polysaccharides. (S. Weiner, Biochem. 22, (1983), 4139–45; C. S. Sikes, A. P. Wheeler, in Chemical Aspects of Regulation of Mineralisation., Eds. C. S. Sikes, A. P. Wheeler University of South Alabama Publ. Services (1988), 15–20).

Unfortunately, both in nature and in the industrial sector, unwanted mineralization processes also occur and result in tenacious, troublesome deposits and encrustations such as, for example, dental plaque, organ concretions or, in the industrial sector, encrustations on heat exchanger surfaces or cooling towers particle agglomerations in pigment dispersions, encrustations on hard (for example glass metal) and soft (textile) surfaces. In the past, various proposals have been made for exploiting this natural action principle for industrial problems. Thus, the U.S. Pat. Nos. 4,534,881, 4,585,560, 4,587,021 describe the inhibition of calcium carbonate deposits by protein fractions, polysaccharide fractions or polyamino acid fractions from calcium carbonate-forming organisms such as crustaceans etc.

In addition, the inhibition of mineral deposits by polyanionic hydrophobic polypeptides with a block copolymer structure and related phosphorylated polypeptides is claimed in the literature (U.S. Pat. No. 4,868,287). The polypeptides used are prepared by methods of peptide chemistry. WO 92/17194 states that an improved synthesis of these polypeptides is provided.

Since the proteins described above acquire their polyanionic characteristics through a high aspartic acid content, aspartic acid homo- and copolymers are also claimed for this purpose. These polyaspartic acids are, however, all obtained by chemical synthesis. Thus, for example, a polyaspartic acid sodium salt can be prepared by thermal polycondensation of aspartic acid to polysuccinimide and subsequent basic hydrolysis. (Kovacs et al. J. Org. Chem, 26 (1961) 1084–1091). Further applications claim the preparation and use of polyaspartic acids by thermal polycondensation of aspartic acid in the presence of acidic catalysts such as phosphoric acid. In addition, polyaspartic acids are also prepared by thermal polymerization starting from aspartic acid precursors such as maleic acid ammonium salt (EP 0 256 366), maleic amide (EP 0604 813) and maleic anhydride, and ammonia-releasing compounds.

BRIEF SUMMARY OF THE INVENTION

The present invention now describes biological methods for producing aspartic acid homo- and copolymers and the use of the resulting polymers for inhibiting mineral deposits and dispersing solid particles.

To date, three different polyamino acids have been found in nature, poly-γ-glutamate, poly-Σ-lysine and poly-α-arginylaspartate (cyanophycin).

Poly-γ-glutamate is produced by various Gram-positive bacteria such as, for example, *Bacillus licheniformis, Bacillus subtilis* natto or *Bacillus anthracis.* poly-Σ-Lysine is produced by *Streptomyces albulus.*

Poly-α-arginylaspartate is produced by many cyanobacteria such as, for example, *Spirulina platensis,* Aphanocapsa PCC 6308 or *Anabena cylindrica.* Synthesis takes place by the non-ribosomal pathway, resulting in a polypeptide which has a polydisperse molecular weight distribution and is stored in the form of cyanophycin granules inside cells.

To date, only the biotechnological production of poly-γ-glutamate using *Bacillus subtilis* or *Bacillus licheniformis* is disclosed in the patent literature. (JP 1-174397 (1989), JP 43-24472 (1969) and U.S. Pat. No. 2,895,882).

DETAILED DESCRIPTION OF THE INVENTION

We have now found that aspartic acid homo- and copolymers can be produced using various cyanobacteria via the intermediate cyanophycin. The resulting polymers have the following structures.

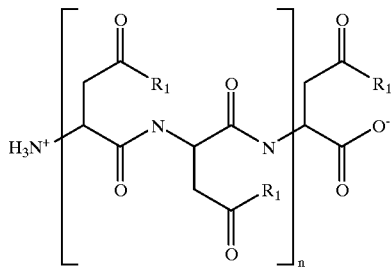

$R_1$: =OH or arginyl n: 5–400

If the total of all the $R_1$ radicals corresponds to 100%, then the proportion of $R_1$=OH is between 5% and 100%, preferably 30%–100% and particularly preferably 70% to 100%. The molecular weight of the polymers is generally between 1000 and 100,000, preferably between 2000 and 50,000, particularly preferably between 2000 and 30,000.

The total n of all repeating units depends on the cleavage conditions to which the intermediate cyanophycin is subjected. Arginine elimination can take place both with acid and with base. If an acidic hydrolysis is carried out, stoichiometric amounts of acid in relation to the incorporated arginine are necessary because the acid is trapped as arginine salt. It is possible to employ as acid all mineral acids such as, for example, hydrochloric acid, sulfuric acids, phosphoric acids and lower fatty acids of $C_1$–$C_5$. The hydrolytic cleavage can moreover take place under pressure using carbonic acid or $CO_2$. Depending on the concentration of the acid employed and on the reaction conditions, depolymerization by hydrolytic cleavage of the polyaspartate chain may also take place, in addition to the arginine elimination. However, the unwanted depolymerization can be minimized by suitable choice of the reaction conditions, such as dilute acid, moderate reaction times, temperatures not exceeding 100° C.

However, the hydrolysis can also advantageously be carried out under basic conditions, because the polyaspartate chain is more stable under these conditions. The reaction is carried out at a pH≧8.5, preferably 9–12, and at temperatures between 20° C. and 150° C., preferably 50° C.–120° C. After the hydrolysis, the reaction product is removed by filtration from the unreacted cyanophycin and the alkali-insoluble arginine. Suitable as base for the alkaline hydrolysis are all metal hydroxides or carbonates which make pH values>8.5 possible in aqueous medium. Alkali metal and alkaline earth metal hydroxides are preferred.

The cyanophycin employed for the hydrolytic formation of the aspartic acid homo- and copolymers is obtained by fermentation of cyanobacteria such as, for example, Aphanocapsa PCC 6308, *Anabena cylindrica* or *Spirulina platensis*. A possible biosynthetic pathway is described in the experimental part.

The aspartic acid homo- and copolymers obtained as products were characterized by elemental analysis, amino acid analysis and NMR spectroscopy. The molecular weight was determined with the aid of aqueous GPC. In addition, for industrial applications, the products were tested for their ability to inhibit mineral deposits such as calcium carbonate, calcium sulfate, calcium phosphate, calcium oxalate and barium sulfate, and for their dispersing capacity for solid particles. The calcium carbonate inhibiting capacity was carried out inter alia by a method of C. S. Sikes, A. P. Wheeler in Chemical Aspects of Regulation of Mineralisation, pp. 53–57, University of South Alabama Publication Series (1988). The products are completely biodegradable owing to their natural polypeptide structure based on α-linked L-aspartic acid.

They can be employed, for example, as cobuilders in detergents and cleaners, for inhibiting and dispersing deposits in cooling and heating circulations for diminishing and dispersing deposits, and for reducing corrosion and inhibiting gas hydrates in petroleum and natural gas production.

EXAMPLE 1

Culture conditions, extraction and purification of cyanophycin:

The cyanobacterium Aphanocapsa PCC6308 is incubated in a 10 l fermenter (batch culture) with 9 l of BGII medium under phototrophic conditions (6000 lux, l/d cycle 12/12) at 30° C. and supplied with air (200 ml/min). Before the cells reach the stationary phase (after 14 days with an optical density $OD_{665}$ of about 1.6), 10 mg/l L-arginine and/or 200 mg/l $NaNO_3$ and 5 mg/ml chloramphenicol are added to the medium, and then the cell suspension is incubated for a further 48 h with reduced light (600 lux) and at lower temperature (20° C.). The cells are harvested by centrifugation at 10 000 xg and washed twice in distilled water. The cell pellet (about 25 g wet weight, about 3 g dry matter) is taken up in 100 ml of an aqueous buffer solution (pH 7.2). The cells are disrupted by ultrasound treatment and then stirred at 4° C. for 15 h. The crude cyanophycin is pelleted by centrifugation at 30 000 xg. The crude cyanophycin is resuspended in 60 ml of $H_2O$. The supernatant (S 1000) obtained by three fractional centrifugations at 1 000 xg is subjected to a centrifugation at 30 000 xg, and the pellet obtained in this way is dissolved in 0.1N HCl (yield: about 1000 mg of native cyanophycin). The native cyanophycin dissolved in 0.1N HCl is finally purified by retritration three times in 1N NaOH (yield: about 150 mg of cyanophycin).

The strain Aphanocapsa (=Synechocystis) PCC6308 was originally isolated in 1949 and *G. C. Gerloff* from a lake in Wisconsin (USA) and was described for the first time by Gerloff et al. in 1950 (Gerloff, G. C., Fitzgerald, G. P. & Skoog, F. 1950. The isolation, purification and nutrient solution requirements of blue-green algae. In Proceedings of the Symposium on the Culturing of Algae, pp. 27–44. Dayton, Ohio, U.S.A.: Charles F. Kettering Foundation).

The strain Synechocystis PCC 6308 used in the present application was deposited in the name of Bayer AG, 51368 Leverkusen, on Feb. 19, 1998 at the DSMZ-Deutsche Sammlung von Mikroorganismen und Zellkulturen GmbH, Mascheroder Weg 16, D-38124 Brunswick with the number DSM 12037.

EXAMPLE 2

Basic hydrolysis of cyanophycin 500 mg of cyanophycin from Example 1 are suspended [lacuna] 5 ml of water. 75 mg of NaOH (100%) are added, and the mixture is heated at 90° C. with stirring for 12 h. The mixture is then cooled to room temperature and filtered. The residue remaining is a mixture of arginine and unreacted cyanophycin. The filtrate contains the sodium salts of the aspartic acid homo- and copolymers.

Determination of the calcium carbonate inhibiting capacity by modification of the NACE[1]) method: TM 0374-90

[1])NACE: National Association of Corrosion engeneers

Starting materials:

Solution 1:

12.15 g of calcium chloride dihydrate, analytical grade 3.68 g of magnesium chloride hexahydrate, analytical grade made up to 1000 ml of solution with distilled water.

Solution 2:

7.36 g of sodium bicarbonate, analytical grade made up to 1000 ml of solution with distilled water.

Solutions 1. and 2. must each be made up freshly and saturated with $CO_2$ before use thereof.

100 ml of solution 1. are mixed with 1,2,3,5,10 ppm inhibitor (active substance) based on the complete test mixture. Then 100 ml of solution 2. are added.

The test mixture is then mixed by shaking in a closed vessel and stored in a waterbath preheated to 70° C. for 16 h. (For comparison, a sample without added inhibitor is included in the test series.) After this time, all the samples are removed simultaneously from the waterbath and cooled to 30° C. 5 ml portions are taken from all the samples, filtered through a 0.45 μm filter and acidified with hydrochloric acid for stabilization.

The calcium content in the filtrate is determined by titration with an indicator or by atomic absorption spectroscopy.

The inhibiting capacity is calculated as follows:

$$\frac{a-b}{c-b} * 100 = \% \text{ inhibition}$$

a: amount of calcium in the sample b: amount of calcium in the blank after heat treatment c: amount of calcium in the blank before heat treatment

| Inhibitor [ppm] | Example 2 | Inhibition [%] Polyaspartic acid chemical synthesis |
|---|---|---|
| 1 | 20 | 44 |
| 2 | 39 | 59 |
| 3 | 66 | 72 |
| 5 | 83 | 85 |
| 10 | 90 | 94 |

We claim:

1. α-linked L-aspartic acid homo- and copolymers obtained by hydrolytic arginine elimination from cyanophycin.

2. Process for producing α-linked L-aspartic acid homo- and copolymers by eliminating arginine from cyanophycin.

3. Process according to claim 2, wherein the arginine elimination takes place under basic conditions.

4. Process according to claim 3, wherein the cyanophycin is produced by fermentation with the aid of cyanobacteria.

5. Process according to claim 3, wherein the cyanophycin is produced by fermentation with the aid of the cyanobacterium Aphanocapsa PCC6308.

6. A method of using the α-linked L-aspartic acid homo- and copolymers according to claim 1 for inhibiting mineral deposits, wherein said method comprises the step of adding the α-linked L-aspartic acid homo- and copolymers to a vessel containing water and dissolved minerals.

7. A method of using the α-linked L-aspartic acid homo- and copolymers according to claim 1 for dispersing solid particles, wherein the α-linked L-aspartic acid homo- and copolymers are added to a vessel containing a dispersion of solid particles in water.

* * * * *